United States Patent [19]

Uemura et al.

[11] 4,361,652

[45] Nov. 30, 1982

[54] METHOD FOR STABILIZING PLASMINOGEN

[75] Inventors: Yahiro Uemura, Hirakata; Katuhiro Uriyu, Sakurai; Satoshi Funakoshi, Katano, all of Japan

[73] Assignee: The Green Cross Corporation, Osaka, Japan

[21] Appl. No.: 225,531

[22] Filed: Jan. 16, 1981

[30] Foreign Application Priority Data

Jan. 25, 1980 [JP] Japan .................................... 55-8072

[51] Int. Cl.³ .......................... C12N 9/96; C12N 9/68
[52] U.S. Cl. .................................... 435/188; 435/217
[58] Field of Search ........................ 435/217, 188, 212

[56] References Cited

U.S. PATENT DOCUMENTS

| | | | |
|---|---|---|---|
| 2,897,123 | 7/1959 | Singher | 435/217 |
| 2,923,665 | 2/1960 | Hagan et al. | 435/217 |
| 3,865,692 | 2/1975 | Holleman et al. | 435/217 |

OTHER PUBLICATIONS

Methods in Enzymology, vol. 19, pp. 184–199, (1970).

*Primary Examiner*—Lionel M. Shapiro
*Attorney, Agent, or Firm*—Cushman, Darby & Cushman

[57] ABSTRACT

A method for stabilizing plasminogen which comprises adding a physiologically acceptable inorganic salt to a plaminogen-containing aqueous solution to give a final concentration of the salt of 0.002 to 0.4 M.

3 Claims, No Drawings

METHOD FOR STABILIZING PLASMINOGEN

The present invention relates to a method for stabilizing plasminogen originated from human blood plasma and also to a stabilized preparation of said plasminogen.

Plasminogen is activated by urokinase or by streptokinase turning into plasmin, which in turn decomposes fibrin into soluble matter, i.e., causes fibrinolyis, so that plasminogen is noted together with urokinase and with streptokinase as a medicine widely available for clincal uses besides for the treatment of thrombosis. It is known, however, plasminogen is inactivated by treatment under severe conditions such as heat treatment or lyophilization or by a long-term storage.

Plasminogen preparations like other blood preparations have the possibility of contamination by hepatitis virus and therefore need a heat treatment at 60° C. for 10 hours in order to prevent the spread of hepatitis due to the contaminated preparations, but plasminogen is inactivated by such a treatment to a great extent when the customary method is applied to this treatment.

As an example of successful heat treatment of plasminogen at 60° C. for 10 hours, the acid treatment method of Sgouris et al. [J. T. Sgouris, Vox Sang., 5, 357 (1960)] is known. This method comprises removing impurities from an aqueous solution of plasminogen by lowering the pH of the solution to a value of 2 under a low ionic strength, thereafter correcting the pH to a value of 3 to 5, and heat-treating at 60° C. for 10 hours. The plasminogen preparation obtained by this method (hereinafter referred to as acid-treated plasminogen) has a drawback of being insolubilized in neutral pH region and therefore unfavorable for medical use.

There are reports that the liquid state stability of acid-treated plasminogen is much lower than that of plasminogen never treated with acid [Norma Alkzaersig, Biochem. J., 93, 171 (1964)] and that plasminogen never treated with acid is relatively stable in an alkaline pH region of 9 to 10 [Y. Abiko, M. Iwamoto, and M. Shimizu. J. Biochem, 64 (6), 743 (1968)]. However, these reports are concerned with investigations on the stability at 37° C. at the highest and revealed nothing about the heat stability under such severe conditions that can inactivate hepatitis virus.

In view of the above, the present inventors made extensive studies, and as a result, have found that, when a particular compound, which was selected from a great number of compounds, is added to an aqueous solution of plasminogen in a specified proportion, plasminogen can be stabilized even under severe conditions such as those of heat treatment or of lyophilizatiion, needless to say, under usual mild conditions. Then, after further studies, they have accomplished the present invention.

An object of this invention is to provide a method for stabilizing a plasminogen-containing aqueous solution.

Another object of this invention is to provie a stabilized plasminogen preparation.

Other objects and advantages of this invention will be apparent from the following description.

According to the present invention, there is provided a method for stabilizing plasminogen originated from human blood plasma by adding a physiologically acceptable inorganic salt as a stabilizing agent to a plasminogen-containing aqueous solution in an effective amount for stabilization, more specifically, to give a final concentration of the salt of 0.002 to 0.4 M.

This invention also provides a plasminogen preparation containing an effective amount of a physiologically acceptable inorganic salt as a stabilizing agent.

Preferred form of the preparation includes aqueous solution and dry powder thereof, particularly lyophilized powder thereof.

The aqueous solutions containing plasminogen originated from human blood plasma which are available in this invention are not particularly limited; for example, the method of this invention can be applied to various fractions containing plasminogen which are separated by the blood plasma protein fractionation method generally used in the production of important physiological preparations such as fibrinogen, γ-globulin, and albumin in human blood plasma.

Also the degree of purification of plasminogen in these aqueous solutions is not particularly limited; for example, the present method can be applied to plasminogen solutions highly purified by affinity chromatography using fixed lysine and also to plasminogen solutions roughly purified like fraction III by the Cohn's low temperature alcohol fractionation method.

Any inorganic salt that is physiologically acceptable can be used in this invention; for example, alkali metal salts (e.g., sodium salts and potassium salts), alkali earth metal salts (e.g., magnesium salts and calcium salts), and ammonium salts of mineral acids such as hydrochloric, sulfuric, boric acids (orthoboric acid, metaboric acid, and tetraboric acid), and phosphoric acids (pyrophosphoric acid, orthophosphoric acid, and metaphosphoric acid) may be used. Preferred examples of these salts are NaCl, KCl, $MgCl_2$, $(NH_4)_2SO_4$, $Na_2SO_4$, $Na_2B_4O_7$, $KH_2PO_4$, $K_2HPO_4$, $NaH_2PO_4$, $Na_2HPO_4$, etc.

The method of this invention is carried out by adding the above stabilizer to a plasminogen-containing aqueus solution to give a final concentration of the stabilizer of 0.002 to 0.4 M, preferably 0.01 to 0.3 M, and most preferably 0.05 to 0.2 M. The dry powder preparations contain 0.01 to 10 w/w% of the above stabilizer.

Plasminogen is liable to be inactivated generally during the production process, particularly during heat treatment or lyophilization, as mentioned above. Consequently, the stabilization method of this invention is preferably applied not only to heat treatment of plasminogen-containing aqueous solution or to lyophilization thereof, but also to all stages of the production process. In case of heat-treatment to inactivate viruses contained in a plasminogen-containing aqueous solution, e.g., heat-treatment at 60° C. for 10 hours, it is desirable to carry out the heat-treatment after adding the stabilizer and making the digestion at 4° to 37° C. at pH 2 to 4 for 20 to 60 minutes.

The stabilizers used in this invention may also be allowed to remain as it is in the preparations after the above-mentioned treatment, the remaining stabilizers also enhancing the stability of plasminogen on standing.

The method of this invention described hereinbefore improves the stability of plasminogen in its production stages including heat treatment, lyophilization, and other operations, thereby minimizing the loss of plasminogen in the production process, and the plasminogen preparations containing said stabilizer which are obtained by this method have high stability on standing: thus, the present invention provides a very favorable method as an industrial process for producing plasminogen preparations. It is a matter of course that the method of this invention can be utilized not only in the production of plasminogen preparations, but also widely in other cases where the stabilization of plasminogen is requested.

The following examples illustrate the effect of the method of this invention, which is however not to be limited to these examples.

EXAMPLES

Fraction III obtained by the Cohn's cold ethanol fractionation method was suspended in an aqueous solution containing 1 w/v% of sodium chloride, and after the suspension was stirred for a moment, the supernatant liquor was removed by centrifugation. According to the method of D. G. Deutsch et al. [Science, 170, 1095 (1970)], the supernatant was poured into a lysinesephalose column to adsorb plasminogen, then impurity proteins were washed away with physiological saltwater, and the plasminogen adsorbed was eluted by use of an aqueous solution (pH 7.0) containing both 0.002 M of ε-aminocaproic acid and 1% of sodium chloride.

After dialyzed against distilled water, the purified plasminogen solution was divided into a large numbre specimens, which were classified into four groups, and these groups were treated under the following different conditions, respectively:

Condition D; various kinds of stabilizers were added to the specimens of this group respectively, and the resulting solutions were heat-treated at 60° C. for 10 hours.

Condition B; various kinds of stabilizers were added to the specimens of this group respectively, the resulting solutions were digested at a pH of 3.0 for 30 minutes, and thereafter they were heat-treated at 60° C. for 10 hours.

Condition C; the specimens of this group were digested at a pH of 3.0 for 30 minutes, and after various kinds of stabilizers were added to the resulting specimens respectively, the resulting solutions were heat-treated at 60° C. for 10 hours.

Condition A; the specimens of this group were subject to no treatment besides addition of various kinds of stabilizers.

Thereafter, the remaining activities of the following samples were determined:

The supernatants of the samples obtained under conditions D, B, C, and A after the pH values of these samples were corrected to 7.0+0.2.

The samples obtained by lyophilizing the solutions obtained under condition B (condition E).

The samples of condition E after standing at 4° C. for 6 months (condition F).

The activity determination were carried out by the casein decomposition method according to the procedure of Sgouris et al. [Vox. Sang., 5, 357 (1960)]. Table 1 shows the remaining activities of the various samples obtained by the treatments under the six conditions, expressed in percentage based on the activity of a never heated, no additive-containing plasminogen preparation assumed as 100%.

TABLE 1

Remaining Activities (%) after Treatments under various Conditions

| Additive (conc) | | Condition A | Condition B | Condition C | Condition D | Condition E | Condition F |
|---|---|---|---|---|---|---|---|
| No additive | | 100 | 27 | 27 | 20 | — | — |
| NaCl | (0.05M) | 100 | 72 | 25 | 23 | — | — |
| " | (0.10M) | 100 | 90 | 30 | 35 | 91 | 90 |
| " | (0.15M) | 100 | 95 | 24 | 25 | 94 | 93 |
| KCl | (0.10M) | 97 | 88 | 32 | 25 | 88 | 87 |
| (NH4)2SO4 | (0.02M) | 97 | 80 | 33 | 35 | 81 | 80 |
| " | (0.05M) | 95 | 95 | 25 | 27 | 93 | 94 |
| " | (0.10M) | 100 | 95 | 25 | 20 | 94 | 93 |
| Na2SO4 | (0.02M) | 98 | 77 | 17 | 23 | 76 | 77 |
| " | (0.05M) | 100 | 85 | 17 | 26 | 84 | 83 |
| " | (0.20M) | 100 | 90 | 20 | 30 | 91 | 90 |
| Na2B4O7 | (0.10M) | 99 | 92 | 20 | 27 | 90 | 89 |
| KH2PO4 | (0.02M) | 95 | 85 | 25 | 24 | 83 | 84 |
| " | (0.05M) | 97 | 96 | 25 | 31 | 94 | 93 |
| " | (0.15M) | 95 | 96 | 27 | 35 | 94 | 94 |
| CH3COONa | (0.10M) | 97 | 40 | 12 | 30 | — | — |
| glucose | (0.10M) | 98 | 15 | 11 | 27 | — | — |
| glycine | (0.10M) | 95 | 17 | 10 | 25 | — | — |
| mannitol | (0.10M) | 98 | 15 | 25 | 25 | — | — |
| sodium citrate | (0.50M) | — | 22 | 10 | 15 | — | — |
| sodium caprylate | (0.10%) | — | 17 | 10 | 20 | — | — |
| polyethylene glycol-4000 | (2.0%) | 98 | 35 | 30 | 25 | — | — |

The results shown in Table 1 are outlined as follows:

Plasminogen solutions just after addition of sample stabilizers, exhibited activities of 95 to 100%, that is, practically no activity increase or no decrease due to sample stabilizers was observed (condition A).

The plasminogen solutions containing the stabilizers selected out in this invention, which were digested at a pH of 3.0 for 30 minutes and further heat-treated at 60° C. for 10 hours, retained activities substantially without being deactivated when pH values thereof were returned to neutral region. In contrast, the plasminogen solutions samely treated but containing no additive or containing acetic acid, glucose, glycine, sodium citrate, sodium caprylate, or polyethylene glycol-4000, when pH values thereof were returned to neutral region, yielded large amounts of insoluble matter and the activities of supernatants thereof were quite low (condition B).

The plasminogen solutions digested at a pH of 3.0 for 30 minutes before addition of stabilizer, even if admixed with the same amount of stabilizers as in condition B, yielded large amounts of insoluble matter after heated or when pH values thereof were returned to neutral region, and the remaining activities of the supernatants were low (condition C).

In case where the heat-treatment was carried out at 60° C. for 10 hours immediately after addition of stabilizer, large amounts of insoluble matters formed when pH values of the solution were returned to neutral region and the remaining activities of the supernatant were low (condition D).

From the above facts, it can be said that before making the heat-treatment at 60° C. for 10 hours it is necessary to carry out the digestion.

The remaining activities of the preparations obtained through lyophilization of the plasminogen solutions treated under condition B were almost in their interity, that is, inactivation due to the lyophilization was scarcely observed (condition E). Further, said lyophilized preparations were stable during 6 months storage at 4° C. exhibiting no activity change (condition F).

It can be noted additionally that the lyophilized preparations exhibiting no decrease in activity were dissolved in injection-purpose distilled water and 1 ml of each solution was injected to a mouse weighting 20±2 g and observation was continued for 7 days, during which abnormal symptom was not observed at all.

What is claimed is:

1. In a method for producing a plasminogen preparation comprising adding a physiologically acceptable inorganic salt to a plasminogen-containing aqueous solution to give a final concentration of the salt of 0.002 to 0.4 M and heat-treating the aqueous solution at 60° C. for 10 hours, the improvement which comprises subjecting the aqueous solution to digestion at 4° to 37° C. at pH 2 to 4 for 2 to 60 minutes before the heat-treatment.

2. A method according to claim 1, wherein said physiologically acceptable inorganic salt is an alkali metal salt, alkali earth metal salt, or ammonium salt of hydrochloric acid, sulfuric acid, boric acid, or of phosphoric acid.

3. A method according to claim 2, wherein said physiologically acceptable inorganic salt is NaCl, KCl, $MgCl_2$, $(NH_4)_2SO_4$, $Na_2SO_4$, $Na_2B_4O_7$, $KH_2PO_4$, $K_2HPO_4$, $NaH_2PO_4$, or $Na_2HPO_4$.

* * * * *